US00PP28981P3

(12) United States Plant Patent
Geibel

(10) Patent No.: US PP28,981 P3
(45) Date of Patent: Feb. 20, 2018

(54) ***PELARGONIUM* PLANT NAMED 'PACPEMARYMEX'**

(50) Latin Name: *Pelargonium peltatum*
Varietal Denomination: Pacpemarymex

(71) Applicant: Elsner Pac Jungpflanzen GbR, Dresden (DE)

(72) Inventor: Martin Geibel, Dresden (DE)

(73) Assignee: Elsner Pac Jungpflanzen GbR, Dresden (DE)

( * ) Notice: Subject to any disclaimer, the term of this patent is extended or adjusted under 35 U.S.C. 154(b) by 15 days.

(21) Appl. No.: 14/999,001

(22) Filed: Mar. 15, 2016

(65) Prior Publication Data

US 2017/0290237 P1 Oct. 5, 2017

(51) Int. Cl.
*A01H 5/02* (2006.01)

(52) U.S. Cl.
USPC ..... Plt./332

(58) Field of Classification Search
USPC ..... Plt./332, 324
See application file for complete search history.

*Primary Examiner* — Susan McCormick Ewoldt
(74) *Attorney, Agent, or Firm* — The Webb Law Firm

(57) ABSTRACT

A new and distinct flowering *Pelargonium* plant with big, double, and stable bi-colored flowers.

1 Drawing Sheet

Botanical classification: *Pelargonium peltatum.*
Varietal denomination: 'Pacpemarymex'.

BACKGROUND OF THE INVENTION

The present invention comprises a new and distinct cultivar of *Pelargonium peltatum* known by the varietal name 'Pacpemarymex'. The new variety was discovered in a planned breeding program in Dresden, Germany in the summer of 2012. The purpose of the breeding program was to develop bi-colored, semi-double flowering Ivy *pelargoniums* (geraniums) with a stable flower pattern. The new variety is the result of a crossing a bulk of different genotypes to obtain big, double flowers with a solid merlot-red color and good heat resistance. Cuttings from a new merlot-red colored *pelargonium* seedling with the best flowering characteristics and best growth habit were then grafted on 'Pacshim' (U.S. Plant Pat. No. 20,975) to transfer the flower pattern of bi-colored stripes of 'Pacshim' to the grafts. When the grafted tips that flowered were also bi-colored, cuttings were made from the scion and planted. The rooted plantings are the source of the new variety named 'Pacpemarymex' that is genetically different from 'Pacshim'.

The new variety is similar to 'Pacpemary' (U.S. Plant Pat. No. 26,634) in trailing habit, leaf size, and flower size. However, 'Pacpemary' only exhibits purple-red (61A) colored petals, while 'Pacpemarymex' has bi-colored petals with white margins and purple-red (61A) colored stripes. The new variety was first asexually reproduced in November of 2012 by cuttings in Dresden, Germany. The new variety has been trial and field tested in Dresden and has been found to retain its distinctive characteristics and remain true to type through successive propagations.

The following characteristics further distinguish the new variety from other *pelargonium* varieties known to the breeder:

Stable, bi-colored flowers;
Big, double flowers;
Strong vigor;

Good trailing habit;
All over season flowering; and
Good heat stability.

DESCRIPTION OF THE DRAWING

The accompanying photographic drawing illustrates the new variety, with the color being as nearly true as is possible with color illustrations of this type.

FIG. 1 illustrates an entire flowering plant of the new variety.

DESCRIPTION OF THE PLANT

The following detailed description sets forth the characteristics of the new cultivar. The data which defines these characteristics were collected by asexual reproductions and carried out in a greenhouse from winter through summer in Dresden, Germany The new variety was grown in a 19 cm pot, with treatment of Cycocel® 720 0.2% five times, and two pinchings. The readings and measurements were taken on a 9-month old plant in a room with a window, but without direct sunlight or artificial light. Color references are primarily to the 1995 edition of The R.H.S. Colour Chart of The Royal Horticultural Society of London.

PLANT

Time to initiate roots (days, temperature): About 21 days at about 18-20° C.

Time to develop roots (days, temperature): About 28 days at about 18-20° C.

Time to produce a finished flowering plant from a rooted cutting: About 12 weeks in a 12 cm container.

*Type.*—Ivy.
*Rooting habit.*—Freely branching roots.
*Form.*—Trailing.
*Height from media surface to top of foliage.*—25 cm.
*Height from media surface to top of flowers.*—34 cm.

*Plant diameter.*—55 cm.
*Vigor.*—Medium.
*Strength* (*need for artificial support*).—Long branches need support in production.
*Branching habit.*—Freely branching.
*Stem.*—Main stem length: 55 cm. Diameter: 6 mm. Color: 148A. Texture: Slightly rough. Pubescence: Light. Internode length: 2.5 cm.
*Lateral branches.*—Length: Primary: 20 cm. Secondary: 10 cm. Diameter: Primary: 4 mm. Secondary: 3 mm. Internode length: 25 mm. Texture: Slightly rough. Pubescence: Light. Color: 144A.
*Foliage.*—Arrangement: Mainly opposite, sometimes alternate. Stipules: Size: Length: 10 mm. Width: 7 mm. Color: 146A. Zone: Location: 2 cm from margin. Color: 200B on young leaves, but is lost after maturity. Size of leaf: Length: 3.5 cm. Width: 6 cm. Shape of leaf (generally): Ivy shaped. Shape of apex: Cuneate. Shape of base: Closed and joined together. Texture: Leathery. Aspect: Glossy. Margin type: Lobed and entire. Pubescence: Upper surface: Very light. Lower surface: Very light. Color: Young leaves: Upper surface: 147A. Lower surface: 146A. Mature leaves: Upper surface: 147A. Lower surface: 146A. Petiole: Length: 35 mm. Diameter: 2 mm. Color: 144A. Veins: Venation type: Palmate. Color: Upper surface: 147A. Lower surface: 144A.

INFLORESCENCE

Bud:
*Stage of development when bud characteristics determined.*—Before color appears.
*Shape of cluster.*—Bell-shaped.
*Diameter of cluster.*—3.5 cm.
*Number of buds per cluster.*—8.
*Shape of individual bud.*—Spindle-shaped to round.
*Length of individual bud.*—10 mm.
*Width of individual bud.*—6 mm.
Natural flowering season: Spring until frost in moderate climates.
Blooming habit: Continuous, with early blooming.
Umbel diameter: 8 cm.
Umbel depth: 5 cm.
Borne: Umbel, flowers on pedicel, pedicel on peduncle.
Inflorescence position: Above foliage.
Number of inflorescences per lateral branch: About 3 at the same time.
Lastingness of an individual flower: 6-10 days.
Florets:
*Form.*—Flat.
*Number per umbel.*—8.
*Diameter.*—45 mm.
*Depth.*—25 mm.
Petals:
*Color.*—Upper surface: Margin and stripes are 61A, fading to approximately NN155C (2007 edition of The R.H.S. Colour Chart) in between. Lower surface: Approximately NN155C (2007 edition of The R.H.S. Colour Chart) with a margin of 64B, more or less no stripes present.
*Shape.*—Obovate.
*Length.*—28 mm.
*Width.*—17 mm.
*Apex shape.*—Round.
*Base shape.*—Attenuate.
*Margin.*—Entire.
*Number per floret.*—13.
*Texture.*—Velvety.
*Tonality from a distance.*—Bi-colored merlot/white.
Petaloids:
*Quantity.*—1-2.
*Shape.*—Irregular.
*Color* (*upper and lower surface*).—64B and approximately NN155C (2007 edition of The R.H.S. Colour Chart).
*Length.*—10 mm.
*Width.*—4 mm.
Pedicel:
*Length.*—25 mm.
*Diameter.*—1 mm.
*Color.*—144A.
Peduncle:
*Length.*—10 cm.
*Diameter.*—3 mm.
*Texture.*—Sticky and a little rough.
*Color.*—144A.
Fragrance: None.
Disease resistance: Unknown.
Temperature tolerance: Good heat stability.
Drought tolerance: Medium.

REPRODUCTIVE ORGANS

Stamens:
*Number* (*per flower*).—8.
*Filament.*—Length: 10 mm. Color: Approximately NN155C (2007 edition of The R.H.S. Colour Chart).
*Anthers.*—Shape: Elongated; short tube. Length: 2 mm. Color: 187A.
*Pollen.*—Color: 171A. Amount: Numerous.
Pistils:
*Number.*—1.
*Length.*—10 mm.
*Style.*—Length: 4 mm. Color: Approximately NN155C (2007 edition of The R.H.S. Colour Chart).
*Stigma.*—Shape: Actinomorphic, 5-6 parted. Color: 187A. Size: 2 mm.
*Ovaries.*—Texture: Pubescence present. Length: 4 mm. Width: 2 mm. Color: 147D.

FRUIT/SEED

Fruit/seed description: None observed.

I claim:

1. A new and distinct variety of *Pelargonium* plant substantially as is herein described and illustrated.

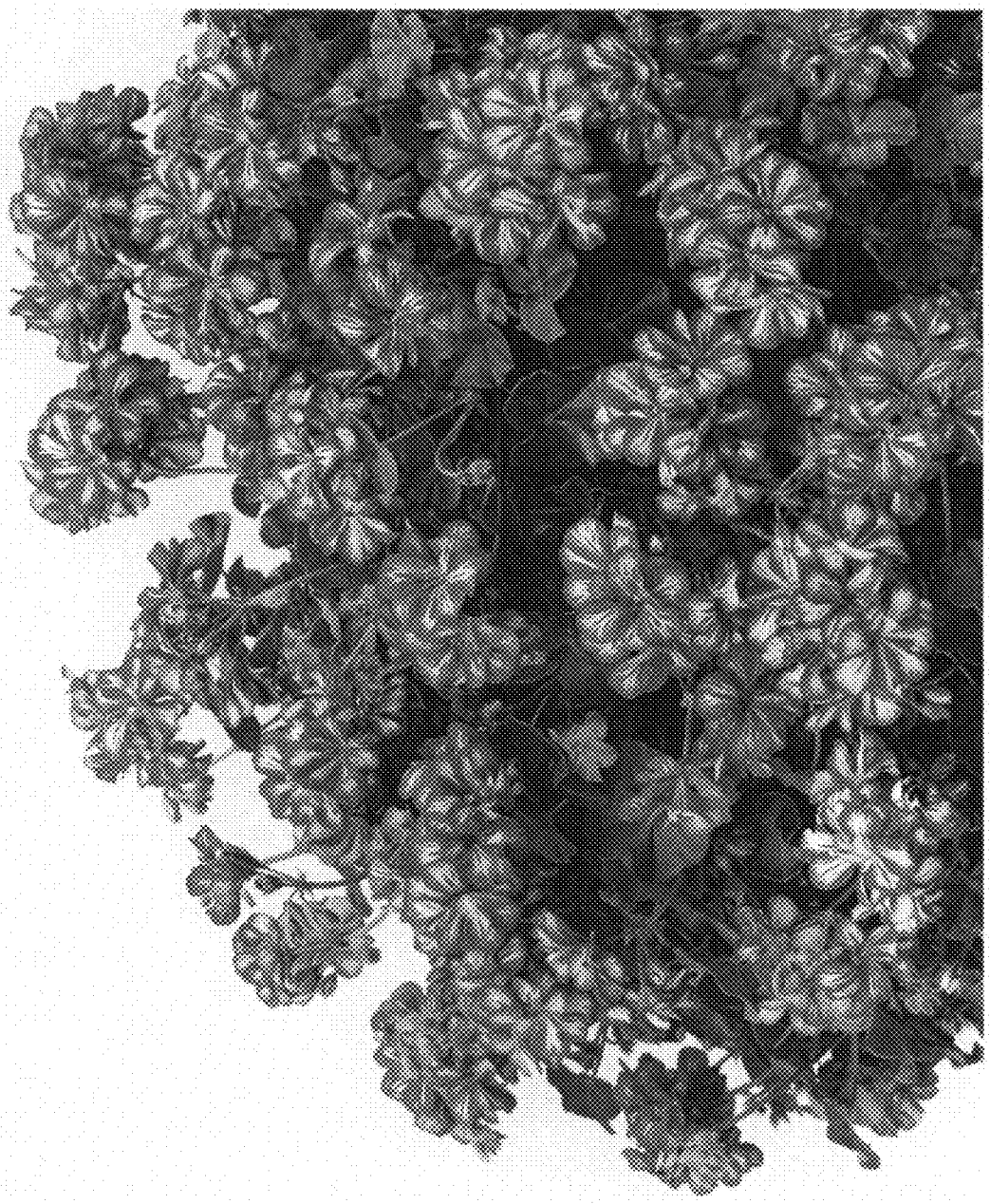

* * * * *